United States Patent
Miga et al.

(10) Patent No.: US 10,426,556 B2
(45) Date of Patent: Oct. 1, 2019

(54) BIOMECHANICAL MODEL ASSISTED IMAGE GUIDED SURGERY SYSTEM AND METHOD

(71) Applicant: VANDERBILT UNIVERSITY, Nashville, TN (US)

(72) Inventors: Michael I. Miga, Franklin, TN (US); Ingrid M. Meszoely, Nashville, TN (US); Rebekah H. Conley, Nashville, TN (US); Thomas S. Pheiffer, Langhorne, PA (US)

(73) Assignee: VANDERBILT UNIVERSITY, Nashville, TN (US)

( * ) Notice: Subject to any disclaimer, the term of this patent is extended or adjusted under 35 U.S.C. 154(b) by 133 days.

(21) Appl. No.: 15/611,492

(22) Filed: Jun. 1, 2017

(65) Prior Publication Data

US 2018/0104010 A1    Apr. 19, 2018

Related U.S. Application Data

(60) Provisional application No. 62/344,300, filed on Jun. 1, 2016.

(51) Int. Cl.
*A61B 34/20* (2016.01)
*A61B 34/10* (2016.01)
*A61B 90/00* (2016.01)
*G06T 7/00* (2017.01)
(Continued)

(52) U.S. Cl.
CPC .............. *A61B 34/20* (2016.02); *A61B 8/085* (2013.01); *A61B 8/5246* (2013.01); *A61B 34/10* (2016.02);
(Continued)

(58) Field of Classification Search
CPC ... A61B 6/547; A61B 90/36; A61B 2034/105; A61B 2090/367; A61B 34/10;
(Continued)

(56) References Cited

U.S. PATENT DOCUMENTS

| | | | | |
|---|---|---|---|---|
| 2004/0019274 A1* | 1/2004 | Galloway, Jr. | ......... | A61B 90/36 600/425 |
| 2004/0059217 A1* | 3/2004 | Kessman | ............. | A61B 8/0841 600/424 |

(Continued)

*Primary Examiner* — Jingge Wu
(74) *Attorney, Agent, or Firm* — Nixon & Peabody LLP

(57) ABSTRACT

A method for image guided surgery includes obtaining intraoperative locations including intraoperative fiducial locations for a non-rigid structure and intraoperative rigid structure locations for associated rigid structures, estimating a gravity deformation for the non-rigid structure based on a first rigid registration for preoperative fiducial locations in a computer model relative to the intraoperative fiducial locations and a second rigid registration for the preoperative rigid structure locations for a rigid structure in the computer model with respect to the intraoperative rigid structure locations, modifying the preoperative fiducial locations using first rigid registration and the gravity deformation, determining a third rigid registration for the modified fiducial locations relative to the intraoperative fiducial locations, calculating a non-rigid transformation for the computer model using the volumetric gravity field deformation and first boundary conditions from errors in the third rigid registration, and displaying image data for the non-rigid structure modified to undergo the non-rigid transformation.

20 Claims, 13 Drawing Sheets

(51) Int. Cl.
*A61B 8/08* (2006.01)
*G06T 7/33* (2017.01)

(52) U.S. Cl.
CPC .............. *A61B 90/36* (2016.02); *A61B 90/37* (2016.02); *G06T 7/00* (2013.01); *G06T 7/33* (2017.01); *A61B 8/0825* (2013.01); *A61B 8/0841* (2013.01); *A61B 2034/105* (2016.02); *A61B 2034/2055* (2016.02); *A61B 2034/2063* (2016.02); *A61B 2034/2065* (2016.02); *A61B 2090/363* (2016.02); *A61B 2090/364* (2016.02); *A61B 2090/367* (2016.02); *A61B 2090/378* (2016.02); *G06T 2207/10028* (2013.01); *G06T 2207/10088* (2013.01); *G06T 2207/10132* (2013.01); *G06T 2207/30068* (2013.01); *G06T 2207/30204* (2013.01)

(58) Field of Classification Search
CPC .................. A61B 34/20; A61B 5/0013; A61B 2034/2065; A61B 8/0825; A61B 8/085; A61B 8/5246; A61B 90/37; G06T 7/00
See application file for complete search history.

(56) References Cited

U.S. PATENT DOCUMENTS

| | | | | |
|---|---|---|---|---|
| 2008/0101673 | A1* | 5/2008 | Fu | G06K 9/32 382/128 |
| 2008/0123927 | A1* | 5/2008 | Miga | G06F 19/00 382/131 |
| 2011/0092793 | A1* | 4/2011 | Thomson | A61B 6/032 600/407 |
| 2012/0330635 | A1* | 12/2012 | Miga | G06T 7/33 703/11 |
| 2014/0044333 | A1* | 2/2014 | Barth, Jr. | G06T 7/0012 382/131 |
| 2014/0241600 | A1* | 8/2014 | Mountney | G06T 17/00 382/128 |
| 2014/0375784 | A1* | 12/2014 | Massetti | H04N 5/23229 348/74 |
| 2016/0038252 | A1* | 2/2016 | Barth, Jr. | A61B 34/25 600/424 |

* cited by examiner

400

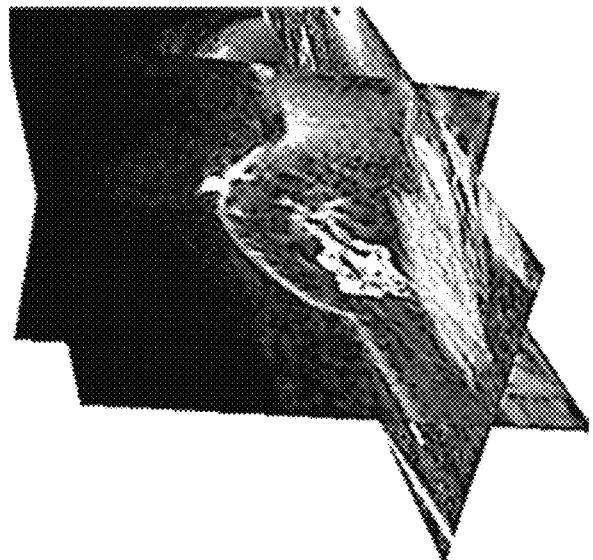
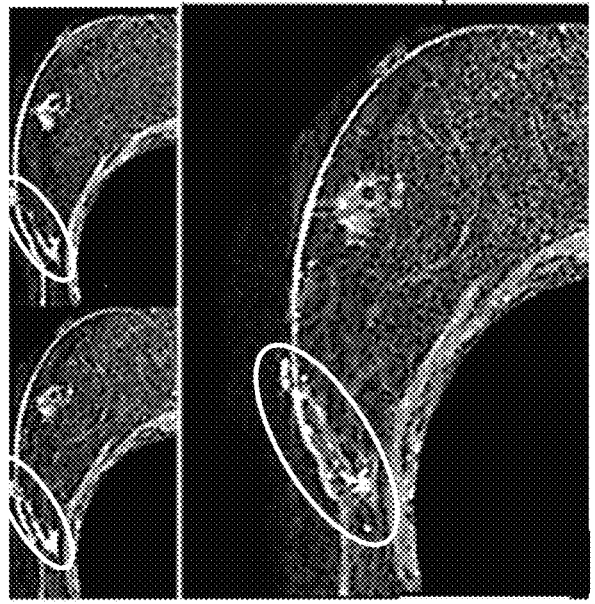
FIG. 6A  FIG. 6B  FIG. 6C  FIG. 6D

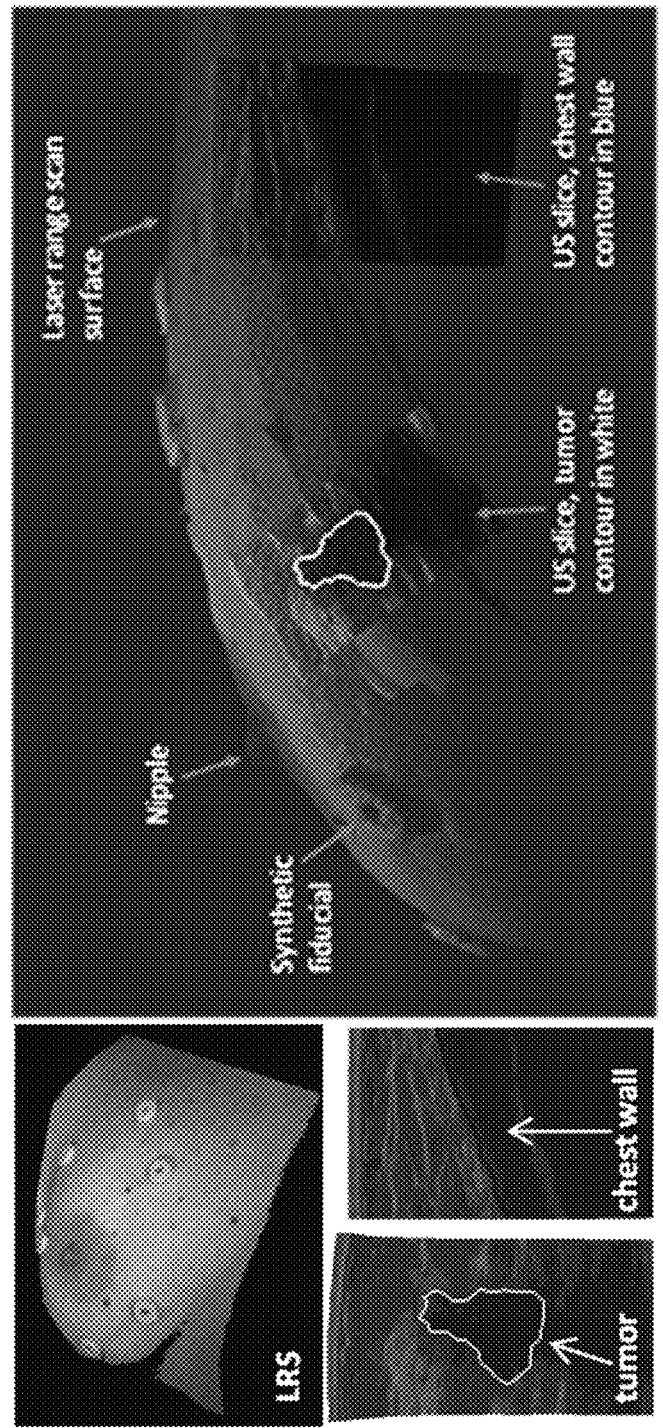

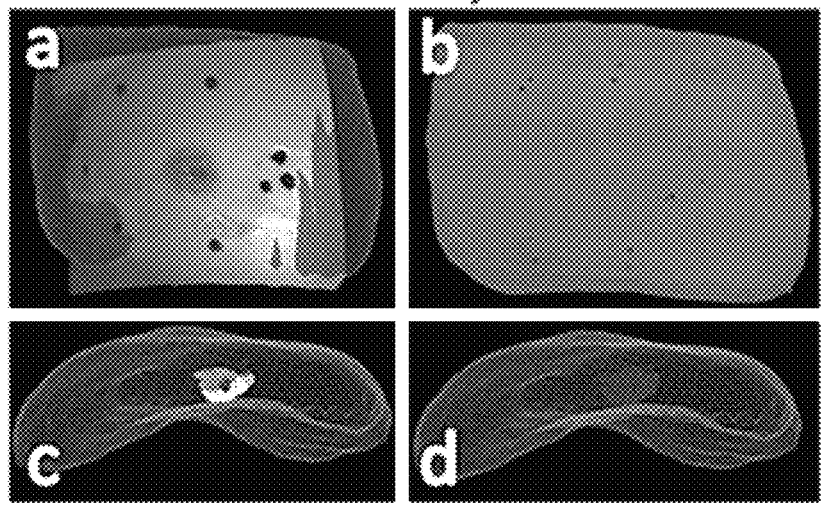
FIG. 10A  FIG. 10B
FIG. 10C  FIG. 10D
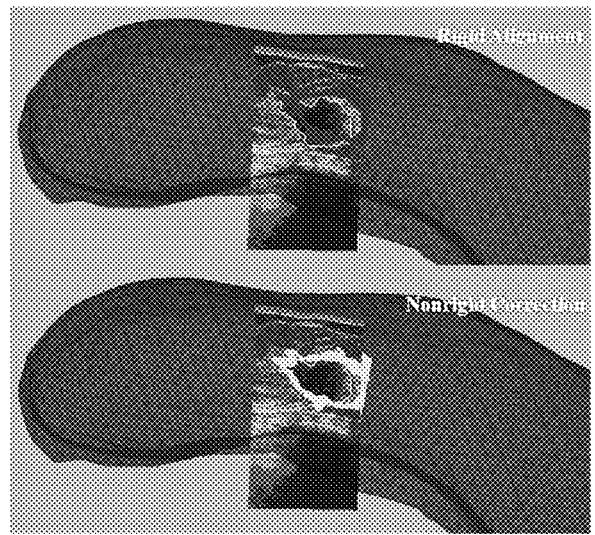
FIG. 11

FIG. 12A   FIG. 12B
FIG. 12C   FIG. 12D
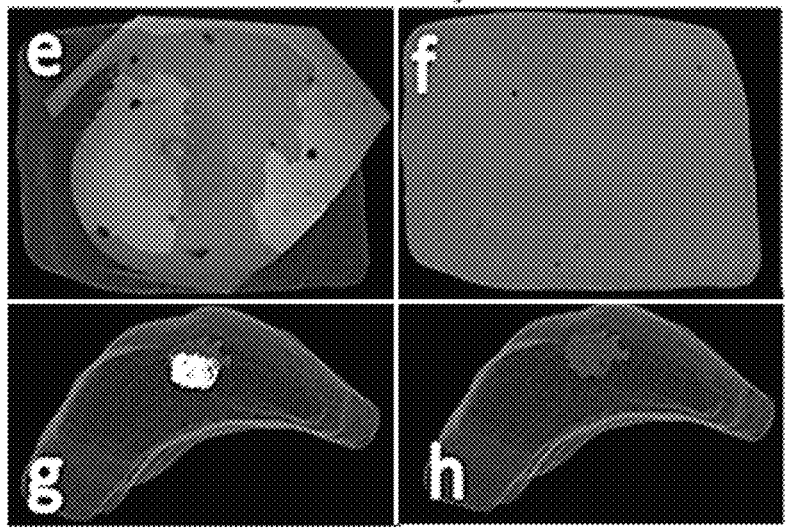
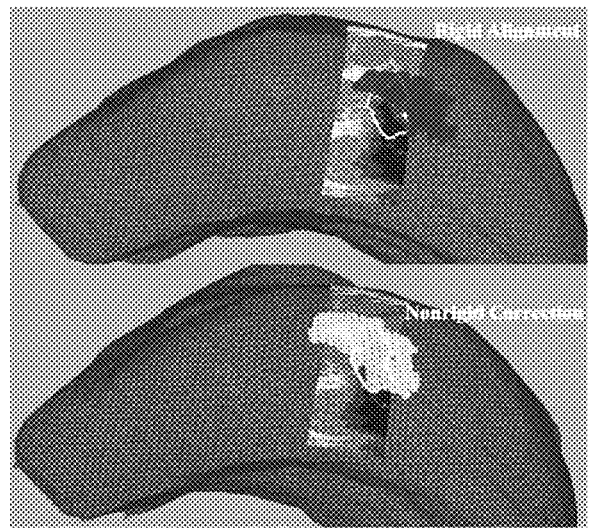
FIG. 13

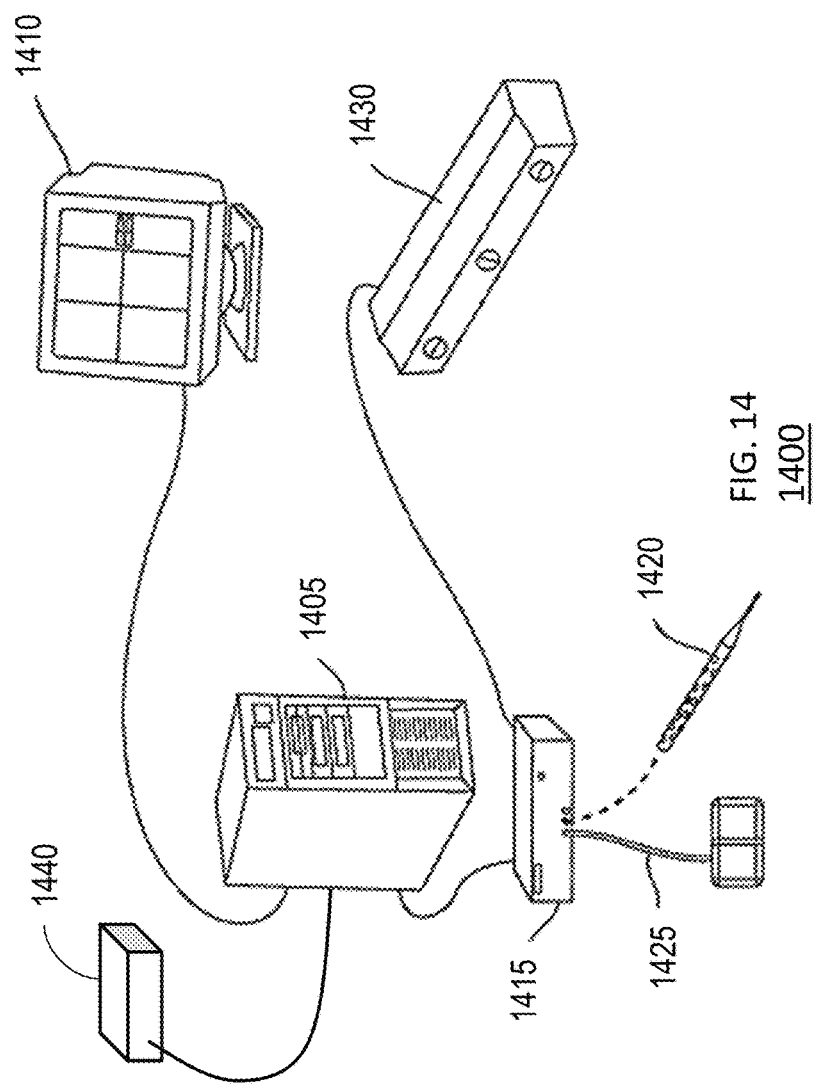

1500

1550

BIOMECHANICAL MODEL ASSISTED IMAGE GUIDED SURGERY SYSTEM AND METHOD

CROSS-REFERENCE TO RELATED APPLICATIONS

This application claims priority to and the benefit of U.S. Provisional Patent Application No. 62/344,300, filed Jun. 1, 2016 and entitled "BIOMECHANICAL MODEL ASSISTED IMAGE GUIDED SURGERY SYSTEM AND METHOD," the contents of which are herein incorporated by reference in their entirety.

FIELD OF THE PRESENT TECHNOLOGY

The present technology relates to image guided surgery systems and methods, and more specifically to systems and methods for biomechanical model assisted image guided systems and methods.

BACKGROUND

Breast cancer is the most frequently diagnosed cancer in women and is also the leading cause of cancer related deaths among women worldwide, with 1.7 million new cases being diagnosed and more than 500,000 deaths occurring in 2012. Breast cancer treatment is dependent upon multimodal therapy with surgery being a primary component, especially for early stage cancers. Mastectomy (total removal of the breast) was the most common procedure choice for newly diagnosed breast cancer patients until the 1980s when studies revealed that lumpectomy, the far less disfiguring option, was shown to have the same 10 year survival rate as mastectomy. Despite this fact, approximately 25-50% of patients eligible for breast conservation therapy (BCT) will choose mastectomy over lumpectomy. A substantial concern of BCT patients is whether or not negative margins will be obtained in the initial surgery. Negative margins are achieved when no cancer cells are present on or near (usually within 5-10 mm) the border of the excised tissue and are considered necessary for a successful lumpectomy. Unfortunately, the current re-excision rates due to positive margins average 20-40% and range from 5-70%. Failure to achieve negative margins can result in the delay of radiation treatment, increase risk for local recurrence, cause psychological and physical stress on the patient, compromise cosmetic results, and increase cost.

The high re-excision rates arise from the difficulty in localizing tumor boundaries intra-operatively and lack of real time information on the presence of residual disease. The challenge in determining surgical margins intraoperatively is that geometric and spatial cues are quickly lost in the surgical presentation. Equally confounding is that valuable diagnostic images are acquired in a significantly different breast presentation than the typical surgical setup. Diagnostic and biopsy information are driven by mammography and preoperative MR images in which the patient is standing or lying prone with pendant breasts, while surgical presentation is in the supine position.

An example of this challenge is displayed in FIGS. 1A-1C, showing that the breast undergoes significant shape change between the prone and supine positions causing the tumor to deform and change location. FIGS. 1A and 1C are axial slices of T1-weighted THRIVE sequence MR images in the prone and supine positions with ovals designating the same tumor in the same axial slice. FIG. 1B shows the intraoperative presentation. As is readily apparent from FIGS. 1A-1C, the changes in patient setup cause the breast tissue, and thus the tumor, to move relative to the MR images. Thus, preoperative MR images have limited value when attempting to locate a tumor intraoperatively.

Current localization strategies used in the operating room (OR) include intraoperative ultrasound, wire guided approaches, and radio-guided occult lesion localization. Prospective studies report that wire guide localization results in positive margins in 38-43% of patients undergoing BCT. Intraoperative ultrasound (iUS) has been shown to improve BCT, but iUS is limited by the fact that only 50% of non-palpable tumors are visible by ultrasound in the breast. The shortcomings of radio-guided occult lesion localization are that the radioisotope must be accurately placed into the tumor and diffusion of the radiotracer into surrounding tissue decreases accuracy of the tumor location. In view of the foregoing, there is a need for accurate intraoperative localization of preoperatively identified tumors and other targets in breast tissues.

SUMMARY

The present technology concerns image guided surgery approach for breast tissues and other similarly configured tissues. In particular, the present technology provides a workflow friendly alignment procedure using rigid and non-rigid registration methods that can be used with both patients not experiencing gross volumetric deformation intraoperatively (small breast volume) and patients experiencing gross volumetric deformation intraoperatively (large breast volume).

In a first aspect of the present technology, a method of performing image-guided surgery is provided. The method includes obtaining intraoperative location data for a patient including intraoperative fiducial location data for a non-rigid structure of interest in the patient and intraoperative rigid structure location data for at least one rigid structure in the patient associated with the non-rigid structure, estimating a gravity deformation for the non-rigid structure of interest based on a first rigid registration for preoperative fiducial location data in a preoperative computer model of the patient with respect to the intraoperative fiducial location data and a second rigid registration for the preoperative rigid structure location data for at least one rigid structure in the computer model with respect to the intraoperative rigid structure location data, modifying the preoperative fiducial location data using first rigid registration and the gravity deformation to yield modified fiducial location data, determining a third rigid registration including a rigid registration for the modified fiducial location data with respect to the intraoperative fiducial location data, calculating a non-rigid transformation for the computer model based on the volumetric gravity field deformation and first boundary conditions derived from errors in the third rigid registration, displaying deformed image data including preoperative image data corresponding to the computer modified to undergo the non-rigid transformation.

In the method, the estimating can include determining a gravity vector rotation based on a comparison of the first rigid registration and the second rigid registration and computing the volumetric gravity field deformation using the gravity vector location and a three-dimensional elastic model. The computing can be a finite element analysis.

In the method, the modifying can include applying a transformation based on the first rigid registration to at least a portion of the computer model corresponding to the non-rigid structure to yield a modified computer model and performing a finite element analysis for the modified computer model based on the gravity deformation and second boundary conditions to yield the modified fiducial data, where the second boundary conditions specify that nodes of the modified computer model associated with the portion and adjacent to the at least one rigid structure are fixed and other nodes of the portion are stress-free.

In the method, the calculating can include performing a principal components analysis (PCA) on the errors in a transformation corresponding the third rigid registration to extract a PCA error vector describing principal components of the errors in the third rigid registration, and computing the boundary conditions based on the PCA error vector. The calculating can also include performing a finite element registration for the computer model with respect to the intraoperative location data subject to the volumetric gravity field deformation and the boundary conditions to yield the non-rigid transformation.

The method can further include, prior to the displaying repeating, using the computer model modified to undergo the non-rigid transformation, the obtaining, estimating, modifying, determining, and calculating.

In the method, the intraoperative location data can include intraoperative shape data for the non-rigid structure, where the computer model includes preoperative shape data for the non-rigid structure, and where at least one of the first rigid registration, the second rigid registration, and the third rigid registration further involve a registration of the preoperative shape data with respect to the intraoperative shape data.

In a second aspect of the present technology, a computer-readable medium is provided, having stored thereon a computer program executable by a computing device, where the computer program including a plurality of code sections for performing the methods of the first aspect.

In a third aspect of the present technology, a system for performing image-guided surgery is provided. The system includes: a digitization system for obtaining intraoperative location data for a patient including intraoperative fiducial location data for a non-rigid structure of interest in the patient and intraoperative rigid structure location data for at least one rigid structure in the patient associated with the non-rigid structure, a display device, a storage medium for storing preoperative computer model of the patient, a computer model of a non-rigid structure of interest in a patient corresponding to the preoperative image, and the surface data, the computer model including a plurality of nodes; and a processing element communicatively coupled to the digitization system, the display device, and the storage medium, wherein the processing element is configured for performing the methods of the first aspect.

BRIEF DESCRIPTION OF THE DRAWINGS

FIGS. 6A, 6B, 6C, and 6D show axial slices of supine MRI of patient volunteer with post-contrast, pre-contrast, contrast-enhanced tumor, and 3D segmentation of the tumor, respectively.

FIG. 8A shows an intraoperative surface scan.

FIG. 8B shows a compression corrected ultrasound image showing the tumor.

FIG. 8C shows an ultrasound image for a chest wall.

FIG. 8D shows a fusion display of tracked intraoperative data.

FIGS. 10A, 10B, 10C, and 10D show registration results for a first patient in accordance with the present technology.

FIG. 11 shows an intraoperative ultrasound image with white tumor contour overlaid on preoperative rigid aligned tumors (Top) and non-rigid corrected aligned tumors (Bottom) in the first patient.

FIGS. 12A, 12B, 12C, and 12D show registration results for a second patient in accordance with the present technology.

FIG. 13 shows an intraoperative ultrasound image with white tumor contour overlaid on preoperative rigid aligned tumors (Top) and non-rigid corrected aligned tumors (Bottom) in the second patient.

FIG. 14 shows an exemplary hardware system configuration in accordance with an aspect of the present technology.

DETAILED DESCRIPTION

Figure 1C:
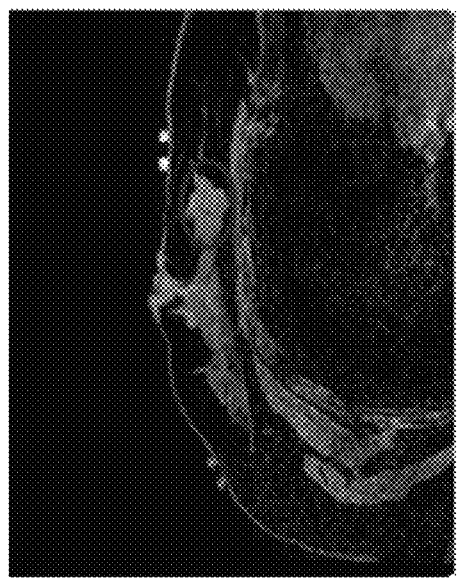
FIGS. 1A and 1C are axial slices of T1-weighted THRIVE sequence MR images in the prone and supine positions with ovals designating the same tumor in the same axial slice and FIG. 1B shows the intraoperative presentation.

The present technology is described with reference to the attached figures, wherein like reference numerals are used throughout the figures to designate similar or equivalent elements. The figures are not drawn to scale and they are provided merely to illustrate the instant present technology. Several aspects of the present technology are described below with reference to example applications for illustration. It should be understood that numerous specific details, relationships, and methods are set forth to provide a full understanding of the present technology. One having ordinary skill in the relevant art, however, will readily recognize that the present technology can be practiced without one or more of the specific details or with other methods. In other instances, well-known structures or operations are not shown in detail to avoid obscuring the present technology. The present technology is not limited by the illustrated ordering of acts or events, as some acts may occur in different orders and/or concurrently with other acts or events. Furthermore, not all illustrated acts or events are required to implement a methodology in accordance with the present technology.

In view of the existing limitations in current technologies for intraoperative localization of preoperatively identified tumors and other targets in breast and similar tissues, the present technology is directed to an improved image-to-physical data alignment framework for improved surgical management.

Figure 2:
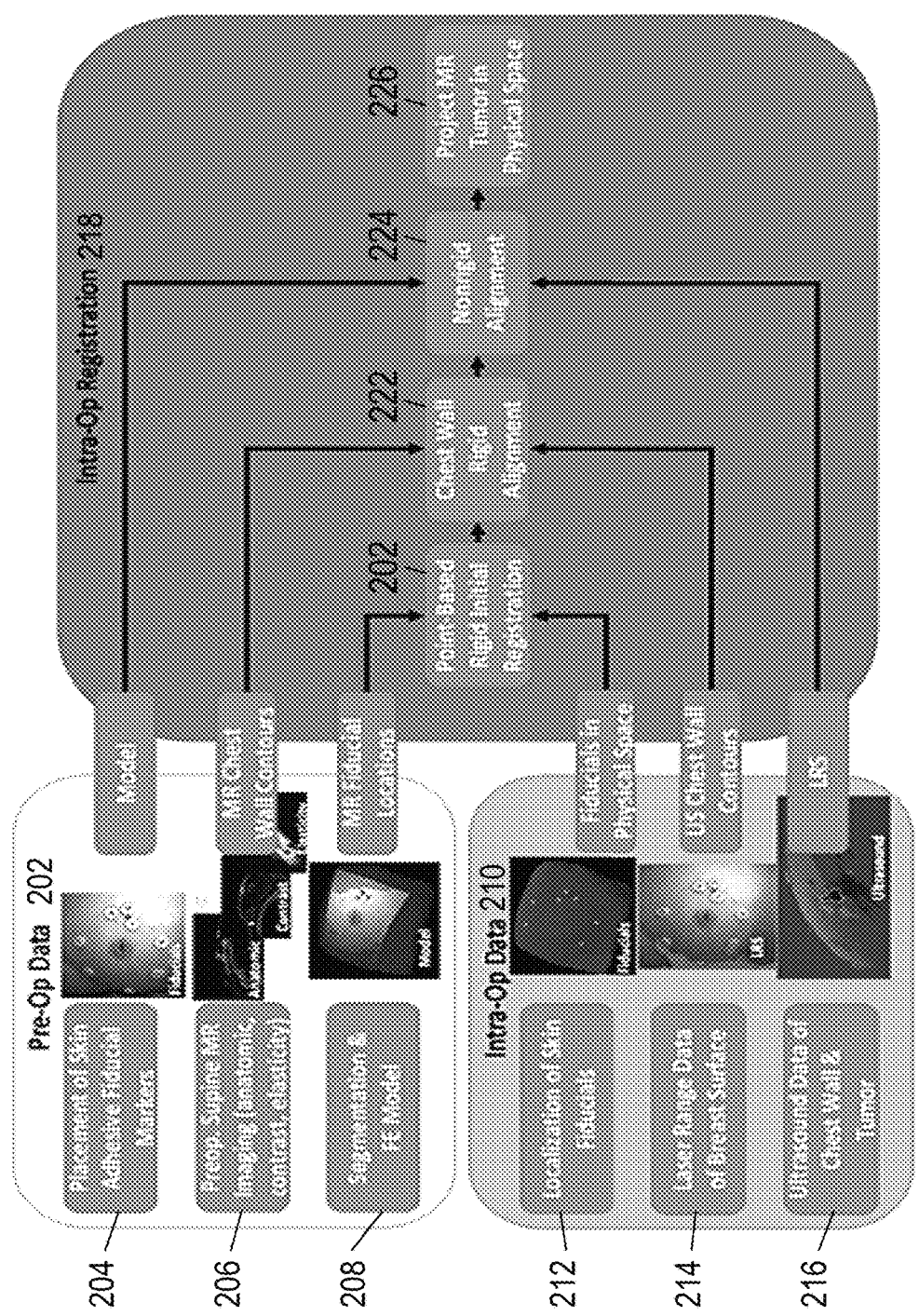
FIG. 2 is a flowchart 200 illustrating exemplary preoperative and intraoperative data collection tasks and a subsequent exemplary intraoperative registration process.

The proposed preoperative and intraoperative collection and processing framework present technology is illustrated with respect to FIG. 2. FIG. 2 is a flowchart 200 illustrating exemplary preoperative and intraoperative data collection tasks and a subsequent exemplary intraoperative registration process.

Briefly, the Preoperative (Pre-Op) Data phase (202) begins with the adherence of MR-visible skin fiducials on the breast (204). It then proceeds to supine MR imaging which currently includes anatomic, contrast enhanced MR, and elasticity images (206). However, the present disclosure contemplates that the imaging can be performed using any other type of imaging technology. This phase can then conclude with segmentation and finite element geometric model construction (208). In some configurations, segmentation can be semiautomatic. However, in other configurations, it can be automatic.

In the Intraoperative (Intra-Op) Data collection phase (210), the process begins with intraoperative localization of the skin fiducials (212). Thereafter, LRS data is obtained for the breast surface (214). Finally, a sparse representation of the chest wall is generated from tracked ultrasound (US) images (216). However, the present disclosure contemplates that the intraoperative data can be collected using any other type of imaging and/or surface data collection technologies.

Next is the Intra-Op Registration phase (218), that begins with a point-based rigid registration (PBRR) using the preoperative and intraoperative fiducial data (220). Once complete, the chest wall of the MR-based geometric model and its sparse counterpart (as determined by US) are compared in physical space to provide a rigid alignment therebetween (222). Using the chest-wall rigid alignment and the fiducial data alignment, a gravity-induced deformation change is applied. Remaining fiducial error is analyzed next. Thereafter, a second non-rigid deformation is applied associated with supine changes between preoperative and intraoperative states (224). Finally, with non-rigid effects accounted for, a final alignment is performed to project the tumor in the preoperative images into physical space, i.e., the intraoperative space (226).

Once the registration of FIG. 2 is completed, the modified computer model, transformed preoperative images, and intraoperative data can be combined in a fused visual display. Intraoperative data can include ultrasound images, physical tracking data, and point clouds. This display can then be further used to guide therapeutic or diagnostic procedures.

Figure 3:
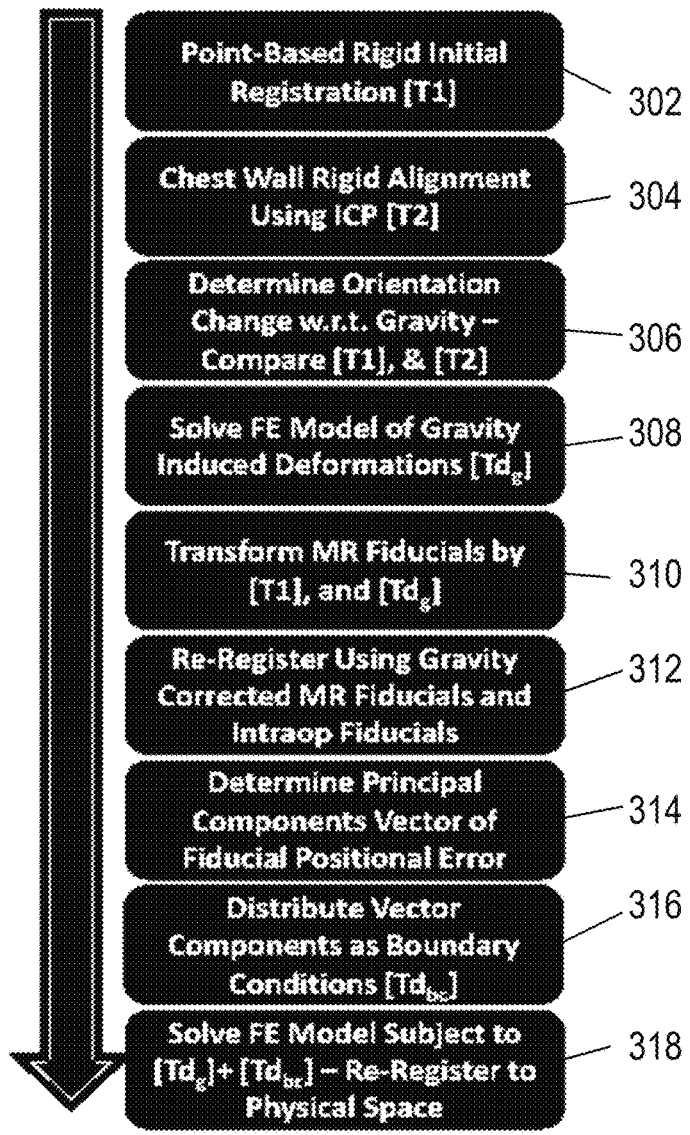
FIG. 3 is a flowchart 300 of steps in an exemplary registration methodology in accordance with the present technology.

The registration methodology of the present technology relies on a strategy in which one decomposes deformation correction into a two component process: gravity-induced changes, and changes due to muscle contractions from ipsilateral arm movement between imaging and surgical presentations. FIG. 3 concisely describes this approach.

FIG. 3 is a flowchart 300 of steps in an exemplary registration methodology in accordance with the present technology. For ease of illustration, the method 300 will be described with respect to breast tissues, but the method 300 can be easily adapted for any other types of tissues associated with skeletal or other rigid structures in the body.

The registration methodology begins with an initial rigid registration of the non-rigid tissues (302). For example, as shown in FIG. 3, a point-based rigid registration (PBRR) of breast tissue images can be performed using synthetic fiducials adhered to the breast. This registration can be used to define a first transformation [T1] for a computer model of the breast. It should be noted that in other configurations, other fiducials can be used instead, alone or in combination with synthetic fiducials. For example, some tissues may have prominent features or structures which can be used as fiducials.

Once the initial registration is complete, a rigid alignment between rigid features of the preoperative and intraoperative images is performed (304). For example, a comparison between the [T1] transformed preoperative MR chest wall and the sparse tracked US-visualized chest wall contours can performed. If significant alignment differences are present after such a comparison, the chest wall features are registered using a standard iterative closest point surface registration so as to define a second transformation, [T2].

The transformation [T2] can be used as an estimate as to how the breast volume has changed with respect to gravity. In particular, to estimate an orientation change with respect to gravity, i.e., to estimate the modified gravitational field for the non-rigid tissues (306). Under this modified gravitational field, a 3D elastic model, such as a Hookean biomechanical model, can be used to estimate the volumetric effect of this body force change on the breast and define a deformation due to gravity $[Td_g]$ (308). This can be computed using boundary conditions that reflect a fixed chest wall and sternum region and stress free boundary conditions on the rest of the breast domain. Based on the deformation $[Td_g]$ and the transformation [T1] corresponding to the initial registration, gravity-shifted fiducial locations are estimated (310), which can then be quickly re-registered to the previously acquired physical space counterparts via a rigid registration process (312).

It should be noted that prior to a final registration, it is also necessary to account for muscle contraction due to arm position. In the exemplary methodology of FIG. 3, this can be done by performing a principal component analysis (PCA) on the difference vectors between co-registered fiducial points to determine the direction of largest remaining deformation (314). The largest principal distance vector can then be used to approximate the magnitude of stretching/compression to establish boundary conditions for the inferior-superior breast surfaces (316). For example, an approximated displacement application can be distributed evenly among the two control surfaces. A final model solution, combining gravity-induced deformation and this approximate stretch/compression, can then be calculated (318) and a final registration between model-corrected MR fiducials and intraoperatively digitized corresponding points can be performed to align the volume. The methodology of FIG. 3 involves only two model solves (at 308 and 318) and therefore provides a fast correction strategy that can be readily adapted to an operating room environment.

In some configurations, an iterative approach can be employed to reconstruct the distribution of displacements by incorporating additional shape conformity metrics based on surface information. As shown in FIG. 2, the pipeline shown therein describes how to transform the geometric information of an MR-depicted tumor into the coordinate space associated with the physical patient for the purpose of localization (this coordinate system is referred to as the physical space). The non-rigid alignment procedure required to perform this projection could include an iterative approach. The iterative method would use the non-rigid procedure described in FIG. 3 as an initial registration to physical space. From here, error calculations would be made using alignment and shape conformity metrics. For example, the fitting of breast surface data collected in the operating room such as by a laser range scanner or swabbing. Geometric points of known correspondence either synthetic or natural/anatomical could also be used. In addition, other geometric data could be used too to include subsurface geometric information as identified by ultrasound or any other imaging modality. The description of the iterative approach is described below.

Iterative Method

1. Establish a best prior estimate for the non-rigid registration (i.e. the result of FIG. 3)
2. Iterate through the following steps
  a. Calculate an alignment error using surface and/or subsurface information (any assessment of geometric misfit with available measurement data)
  b. Check if the alignment error is acceptable within a pre-defined error tolerance or if a number of iterations have already occurred
    i. if acceptable: stop iteration and display results
    ii. if unacceptable: update boundary conditions (displacement or force distributions), solve forward model, and start back at (a).

The deformation and transformations calculated in the iterative routine would be used in the framework (FIG. 2) during the non-rigid alignment block (224).

Details of Registration Methodology

Figure 4:
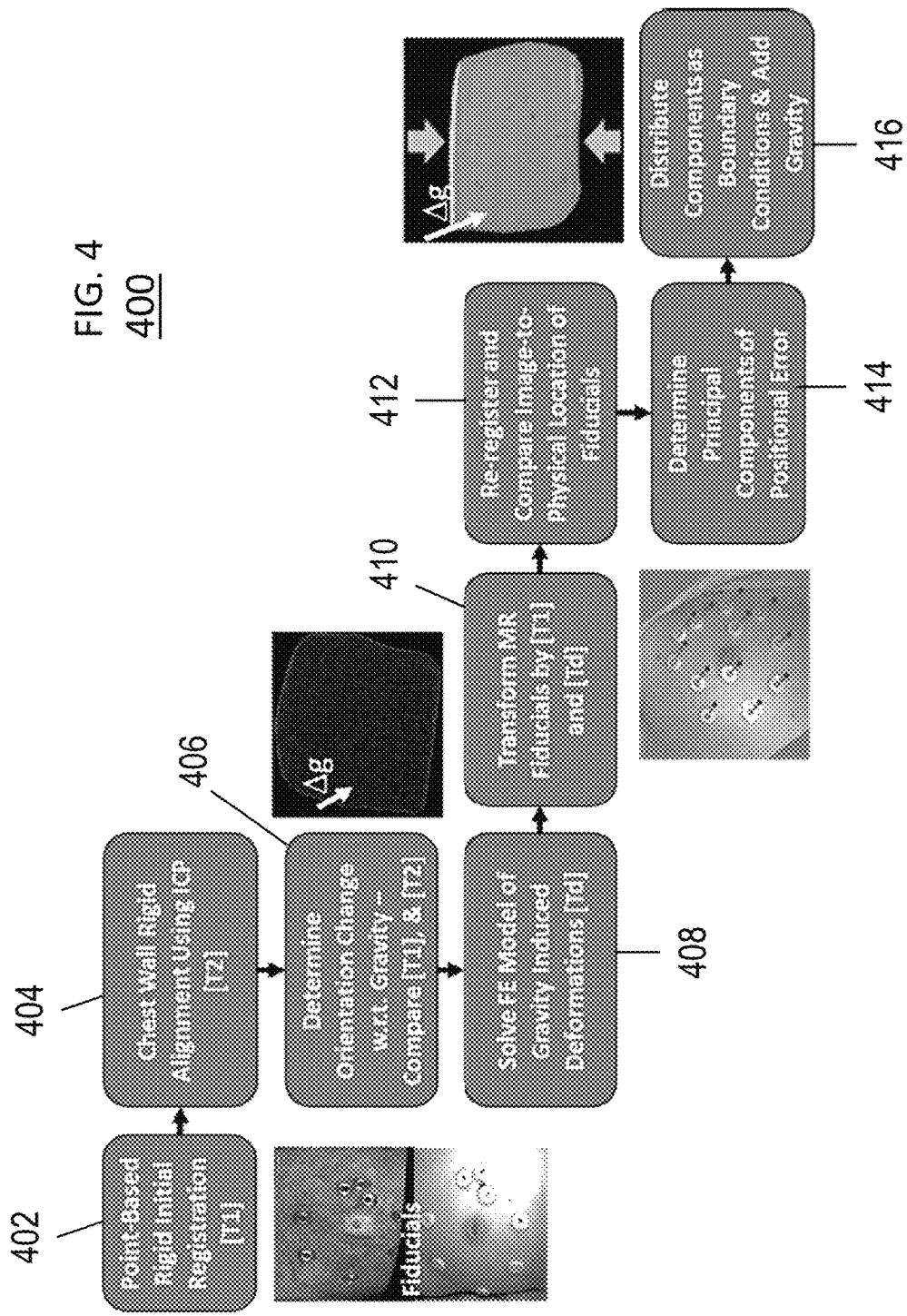
FIG. 4 shows the registration process beginning with rigid initialization and concluding with full non-rigid model compensation.

Turning now to FIG. 4, further details of the registration process of the present technology will be described. FIG. 4 shows the registration process beginning with rigid initialization and concluding with full non-rigid model compensation. As discussed above with respect to FIG. 3, the process of FIG. 4 includes an initial rigid alignment being performed using the synthetic fiducials adhered to the breast. Once complete, a series of steps is conducted to estimate the influence of gravity-induced and ipsilateral arm position changes between supine imaging and surgical configurations. The influence of these variables is then realized as a gravitational inducing body force and boundary conditions which are applied to a biomechanical model of the breast. Once complete, the combined rigid and non-rigid transformation provides a means to map preoperative tumor locations into physical space which can then be subsequently compared with a separate independent ultrasound identified tumor localization.

Initial Rigid Alignment (402). An initial rigid alignment can be performed by registering the MR-digitized marker locations to their intraoperative counterparts. In some aspects, this can be done using a traditional 3D point based singular value decomposition registration algorithm. The point based registration algorithm finds the optimal translation and rotation to minimize the fiducial registration error (FRE) as defined by:

$$FRE = \frac{1}{N}\sum_{i=1}^{N}(R(x_i + \Delta x_i)) + t - (y_i - \Delta y_i) \quad (1)$$

where $x_i$ and $y_i$ are 3×1 vectors of corresponding points in two spaces, $\Delta x_i$ and $\Delta y_i$, are the fiducial localization errors for each point in the two spaces, N is the total number of fiducials, R is a 3×1 rotation matrix and t is a 3×1 vector containing displacements. The resulting translation vector and rotation matrix are applied to the preoperative data to provide an initial alignment with the intraoperative space. However, the present disclosure contemplates that any other rigid registration methods can be utilized.

Quantification of Gravity-induced Deformations (404 and 406). Based on initial studies investigating the use of point-based registration of skin fiducials, the inventors found that significant rotation of the breast occurs relative to the chest wall between supine imaging and intraoperative presentation in some cases. This results in a gravity-induced deformation whereby the breast becomes free to move under the influence of gravity. To estimate this change, the present technology provides a novel strategy in which preoperative and intraoperative chest wall locations, or the locations of any other rigid structures in the patient, are also considered in order to discern the influence of gravity. For example, in some aspects, the preoperative chest wall is designated from the preoperative supine images during a breast model building process and the intraoperative chest wall contours are identified and segmented from a tracked ultrasound examination. Using the fiducial-based registration (at 402) as an initial configuration for transforming the preoperative chest walls, a rigid registration of the intraoperative and preoperative chest walls is performed (404). In particular aspects, the rigid registration can be performed using a traditional iterative closest point (ICP) registration process between the transformed preoperative chest wall points and the intraoperative chest wall contours as digitized by tracked iUS. The rotation matrix resulting from the ICP registration can then applied to the intraoperative gravity vector (assumed to be in the direction normal to the patient's bed). Details of this approach are outlined in Algorithm 1.

Algorithm 1: Algorithm for finding gravity-induced deformations using ICP registration.
1. Initialize by transforming preoperative chest wall contours to intraoperative space using transformation corresponding to initial rigid alignment.
2. Perform an ICP registration between MR chest-wall surface and iUS chest wall contours (404).
3. Extract the rotation matrix from the final transformation and apply to the gravity vector in intraoperative space (406):

$$\Delta g = R^* g_{intraop} \quad (2)$$

where $g_{intraop}$ is a 3×1 vector containing the unit direction normal to the patient bed in intraoperative space.

Mechanics-based Non-rigid Correction (408). Deformations due to gravity-induced changes derived from Algorithm 1 and tissue migration of the breast due to ipsilateral arm movement are estimated using a 3D linear elastic model (408). The model employs the Navier-Cauchy equations and generates a displacement field for correction and is shown here:

$$\nabla \cdot (G\nabla u) + \nabla\left(\frac{G}{1-2v}(\nabla \cdot u)\right) + \rho(\Delta g) = 0 \quad (3)$$

where v is Poisson's ratio, G is the shear modulus of elasticity, u is the 3D displacement vector, ρ is the tissue density, and Δg is the change in gravitational acceleration constant with respect to imaging and surgical presentations. Equation 3 can be solved using the Galerkin Method of Weighted Residuals with linear Lagrange polynomials defined locally on the tetrahedral elements as the supporting basis and weighting functions. Solving this system results in displacement vectors defined at each node that satisfy static equilibrium conditions. The displacements are then applied to deform the preoperative mesh. In one exemplary configuration, a modulus of 1 kPa, tissue density of 1000 kg/m³, and Poisson's ratio of 0.485 can be applied for the whole breast volume.

First Model Solve-Application of Gravity-induced Deformations. Gravity induced deformations can be simulated by supplying the elastic model with a body force of tissue weight based on the change in acting gravity direction (as determined at 408). One can again assume that the chest wall is a rigid fixed structure. Therefore, the boundary conditions applied to this model solve imposed fixed chest wall nodes (zero displacement) with stress-free boundary conditions elsewhere. The displacements generated from this model solve were applied to the preoperative mesh and used to estimate the remaining positional error of fiducial targets (410).

Final Model Solve (412-416). Non-rigid deformations of the breast due to ipsilateral arm movement were accounted for by applying Dirichlet boundary conditions at control surfaces along the inferior-superior surfaces of the model mesh based on preoperative imaging data. The nodes corresponding to the chest wall and the medial breast face were fixed. The medial breast face was fixed because negligible movement occurs around the patient's sternum. The remainder of the breast surface was designated as stress free.

Figures 5A, 5B, 5C, 5D:
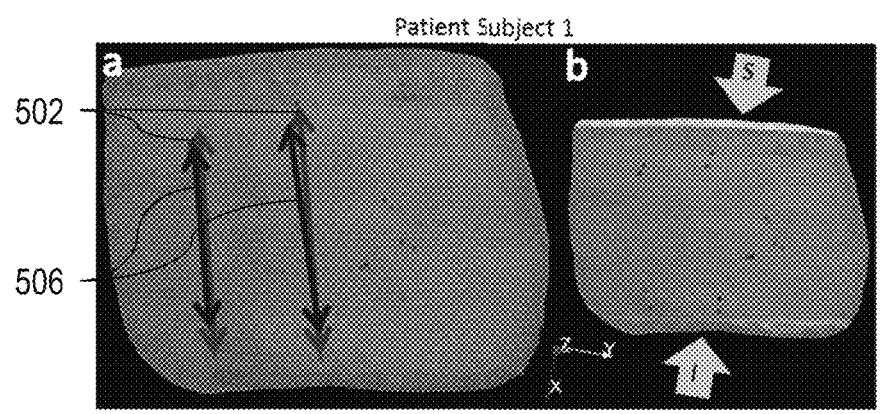
FIGS. 5A, 5B, 5C, and 5D illustrate stretching phenomena observed in intraoperative tissues.

The locations, direction and magnitude of the applied Dirichlet boundary conditions were determined by analyzing the misalignment between the co-registered surface fiducials after gravity-induced changes were taken into account (412). Stretching of the breast between preoperative and intraoperative states was quantified to supply the model with displacement boundary conditions at the inferior-superior tissue cross-sections. When the intra-fiducial distance between two points in the preoperative set is larger than the intra-fiducial distance between the same two points in the intraoperative fiducial set, stretching of the breast tissue has occurred in the preoperative state. This stretching phenomenon is illustrated with in FIGS. 5A-5D in which FIGS. 5A and 5C show that the preoperative intra-fiducial distances for two patients (arrows 502 and 504, respectively) are larger than the intraoperative intra-fiducial distances (arrows 506 and 508, respectively).

One relatively simple approach to correction is to perform a principal component analysis (PCA) on the difference vector between the co-registered fiducial points to determine the direction in which the largest deformation has occurred (414). PCA is performed after the displacement field from the first model solve has been applied to the preoperative FE mesh and re-registered using the new locations of the preoperative fiducials (412). The largest difference in the preoperative and intraoperative intra-fiducial distances along the axis of largest deformation was used to approximate the magnitude of stretching/compression. The approximated magnitude can then be distributed evenly among two control surfaces (416).

Thus, as illustrated above, the proposed registration method requires only two model solves, providing a fast correction strategy that can be readily adapted in the operating room. Given the nature of breast deformation and the reduced domain of the breast analyzed, this methodology is purposefully designed to be workflow friendly, operationally robust, and constrained to establish a baseline understanding of efficacy.

Registration Assessment. Surface markers can be used to quantify registration accuracy by calculating the root mean square fiducial registration error (FRE). FRE is a measure of overall misalignment between fiducials and captures fiducial localization errors as well as non-rigid movements. It is important to note that fiducial location differences between image and physical space would not used as direct displacement boundary conditions in the model, but only as a measure of fit with respect to applied deformations from gravity-induced changes and inferior-superior control surfaces. With respect to subsurface targeting accuracy, tracked ultrasound image contours of the tumor can be compared to their registered preoperative counterpart. For example, the centroid location of the preoperative segmented tumor can be mapped by the process shown in FIG. 4 and compared to the centroid location of the appended 3D tracked iUS tumor contours (note that the contours would be corrected for ultrasound probe deformations). The Euclidean distance ($l_2$-norm) between the intraoperative tumor centroid ($C_{intraop}$) and preoperative tumor centroid ($C_{preop}$) can then be used to measure target registration error: Centroid Difference=$\|C_{intraop}-C_{preop}\|$.

EXAMPLES

The examples shown here are not intended to limit the various aspects. Rather they are presented solely for illustrative purposes.

Preoperative Data Collection

Supine MR Imaging. To evaluate the methods discussed above, preoperative supine MR images were acquired for each patient and were used to create patient specific biomechanical models of the breast tissue, chest wall, and tumor. MR visible adhesive skin fiducial markers (IZI Medical Products, Owing Mills, Md.) were placed over ink markings distributed across the breast surface. The patient was then carefully positioned in a closed bore 3T Achieva MR scanner (Philips Healthcare, Best, The Netherlands). A 16-channel sensitivity encoding (SENSE) torso coil was situated carefully as to not deform the breast, and the ipsilateral arm was placed above the patient's head to more closely replicate surgical presentation. High resolution anatomical images were acquired with a T1-weighted, 3D turbo field echo sequence with fat suppression, a field of view of 200×200×160 mm³, and a reconstructed voxel size of 0.391×0.391×1 mm³.

In some cases, this acquisition can involve acquisition of contrast enhanced supine images. An example of a contrast enhanced image volume of a patient volunteer is shown in FIGS. 6A-6D. In particular, FIGS. 6A, 6B, 6C, and 6D show axial slices of supine MRI of patient volunteer with post-contrast, pre-contrast, contrast-enhanced tumor, and 3D segmentation of the tumor, respectively. In each of FIGS. 6A-6D, an oval identifies the tumor. For the patient subjects studied herein, tumors were identified from the diagnostic MR supine images and were segmented semi-automatically.

Figure 7C:
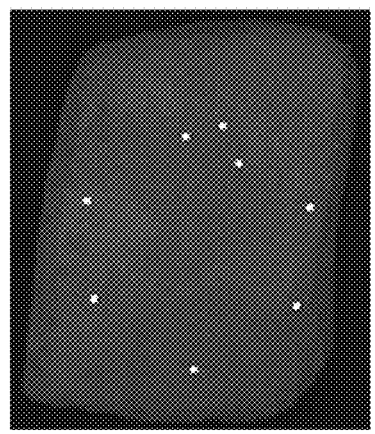
FIGS. 7A, 7B, and 7C, which show segmentation of glandular tissue, a volume render of the supine MR image, and a preoperative mesh showing location of fiducial centers, respectively.
Figure 7B:
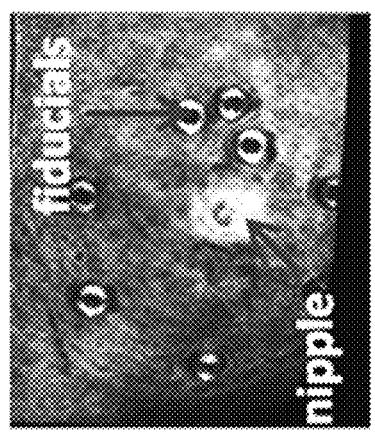
Figure 7A:
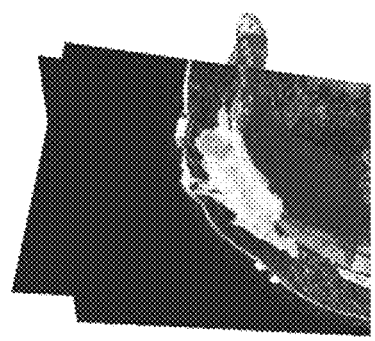

Patient Specific Model. The supine image volume from each patient was segmented into breast tissue, tumor, and chest wall (pectoral muscle) using a semi-automatic segmentation technique by Insight Registration and Segmentation Toolkit (ITK)-SNAP. The segmentation is illustrated in FIGS. 7A-7C, which show segmentation of glandular tissue (FIG. 7A), a volume render of the supine MR image (FIG. 7B), and preoperative mesh showing location of fiducial centers (FIG. 7C).

As noted above, FIG. 7A illustrates the segmentation step for patient 1. The locations of the synthetic fiducial center points were manually determined and recorded (FIG. 7B). Following segmentation, a binary mask of the whole breast was used to generate an isosurface using a standard marching cubes algorithm. The isosurface was then smoothed with a radial basis function using FastRBF Toolbox (Farfield Technologies, Christchurch, New England). From this surface, a finite element tetrahedral mesh was generated using a custom mesh generator with a mesh edge-length resolution of approximately 3 mm (FIG. 7C).

Mock Intraoperative Data Collection. Prior to surgery, a mock intraoperative setup to collect intraoperative data was performed for each patient. Mock intraoperative data was collected to avoid workflow disruptions in the OR and was performed on the same day as preoperative imaging to minimize patient volunteer time. The true intraoperative scenario would involve intraoperative data, such as that shown in FIGS. 8A-8D, to be collected during surgery.

FIG. 8A shows an LRS scan of the patient 2 breast. FIG. 8B shows a compression corrected ultrasound image with tumor contour in white. FIG. 8C shows an ultrasound image with chest wall contour darkened. FIG. 8D shows a fusion display of tracked intraoperative data containing a textured point cloud, adhesive fiducial markers, tracked ultrasound images, tumor contour (white), and chest wall contours (darkened).

To address realistic patient conditions in the mock setup, positioning was performed by a surgical oncologist, to accurately depict OR positioning. Once complete, skin fiducials are digitized with an optical stylus, a laser range data is acquired, and an ultrasound examination is performed. In the following subsections, the extent of this data and its integration is explained.

Surface and Feature Digitization. A custom-built, optically tracked laser range scanner (Pathfinder Technologies, Inc, Nashville, Tenn., USA) was used to digitize the breast surface by sweeping a laser line over the breast surface and recording geometric points along with color information of the visible field, yielding a textured point cloud with known 3D coordinates in physical space. The physical space points corresponding to the MR visible fiducial center points are determined by the black ink markings that were placed on the patient's skin prior to adhering the MR visible fiducials. An optically tracked stylus was used to collect the location of the ink markings. The textured point cloud was used to confirm the location of the fiducial points by com-paring the coordinates collected by the tracked stylus with the field of view color texture information collected from the laser range scanner. All geometric measurements were made with a Polaris Spectra (Northern Digital, Waterloo, ON, Canada) optical tracking system.

Ultrasound Exam. The ultrasound portion of this study was performed in two parts: (1) target B-mode imaging of tumor and (2) chest wall swabbing. Ultrasound images were acquired using an Acuson Antares ultrasound machine (Siemens, Munich, Germany) using a VFX13-5 linear array probe set at 10 MHz. The depth was set at 6 cm to maintain visibility of the chest wall throughout the exam. A passive optically tracked rigid body was attached to the ultrasound transducer. The tracked ultrasound was calibrated using a method that takes multiple b-mode ultrasound images of a tracked stylus tip in the imaging plane to develop a rigid transformation between the image plane and physical space. Once calibrated, all pixels in the ultrasound plane have a corresponding 3D coordinate in physical space. Chest wall contours and tumor borders were semi-automatically segmented using a custom implementation of the Livewire technique.

As known to those of ordinary skill in the case, a Livewire technique performs segmentation based on user selected seed points, automatic extraction of image edges, a lowest cost path algorithm. However, in the various embodiments, any variations of the Livewire technique or any other type of segmentation methods can be used including any other manual, automatic, or semi-automatic techniques. Further, such segmentation methods can be based on image intensity information, thresholding, cost functions, geometric information, global shape assumptions, and statistical models, to name a few.

Figure 9:
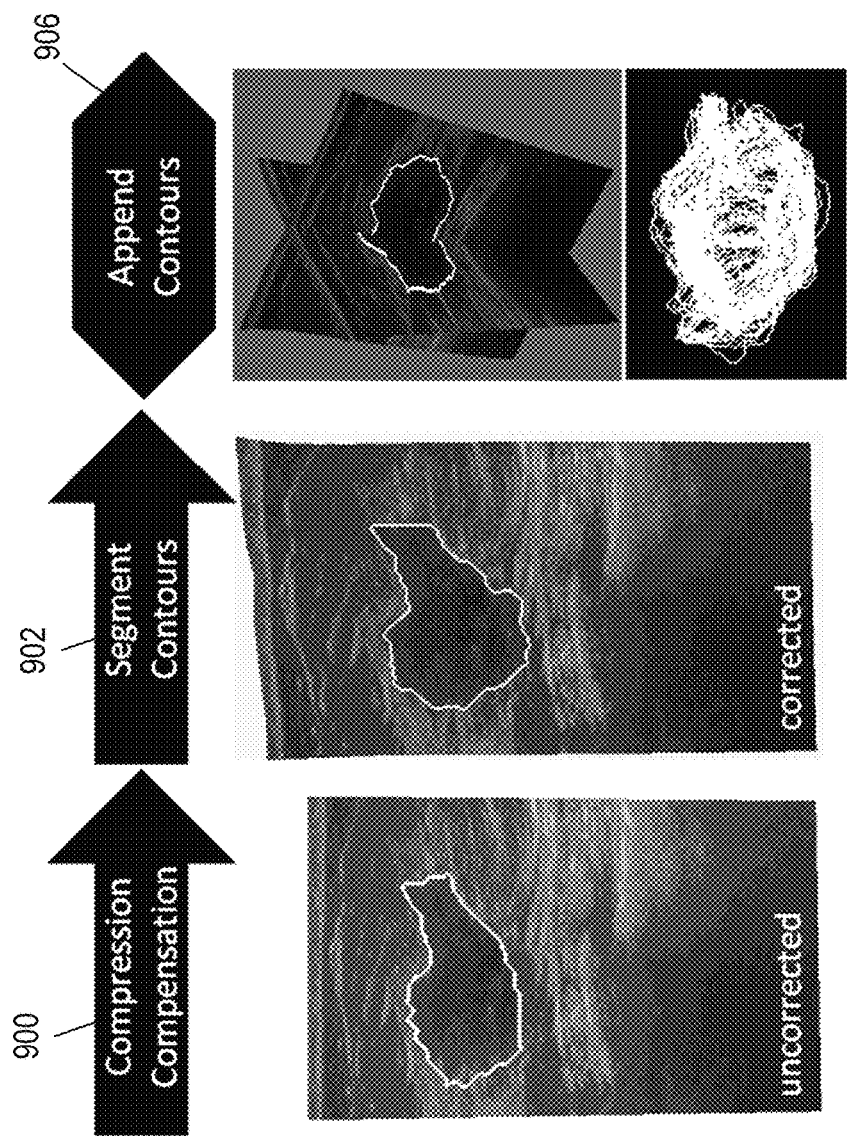
FIG. 9 shows a visual overview of the processing steps involved in acquiring the intraoperative tumor volume.

These 2D segmentations are then appended together to form a 3D sampling of the tumor volume and chest wall in the intraoperative space. FIG. 9 provides a visual overview of the processing steps involved in acquiring the intraoperative tumor volume. The ultrasound images are first corrected for tissue compression exerted by the ultrasound transducer (900). The tumor contour is then segmented in each 2D slice (902). Lastly, all contours are appended to form a 3D representation of the intraoperative tumor (904).

Breast tissue is often compressed during the ultrasound exam by the ultrasound transducer in order to maintain acoustic coupling causing the tissue beneath the probe to deform. Since preoperative supine images were acquired without this compression, a correction scheme was used to transform all ultrasound images of the echogenic tumor into an uncompressed state. As reported in the literature, the fidelity of the method demonstrated reduced subsurface localization errors due to ultrasound probe compression by 67.8% and 51.6% in phantom and clinical experiments respectively. In this study, it was particularly important to utilize these methods as tumor localization is serving as the primary means for accuracy evaluation of our platform.

Patient 1 Results. The initial rigid alignment for patient subject 1 using synthetic fiducials yielded an FRE of 7.5 mm. The centroid difference between the mapped preoperative and intraoperative states before ultrasound probe compression correction of the intraoperative tumor was 7.5 mm. After probe-to-tissue compression compensation, the centroid difference was 6.5 mm. The intraoperative textured point cloud is shown in FIG. 10A with the co-registered preoperative mesh shown in FIG. 10B. The ultrasound compression corrected and uncorrected tumor contours can be compared in FIGS. 10C and 10D. The iterative closest point registration of the intraoperative and preoperative chest-walls revealed that negligible rotation of the torso occurred for patient 1. Therefore, a gravitation body force was not applied. Principal component analysis of the difference in preoperative and intraoperative fiducial locations revealed that the largest deformations occurred along the inferior-superior axis. Intra-fiducial distances along this axis were calculated for patient subject 1 and the maximum difference between preoperative and intraoperative intra-fiducial distances was 20 mm. The difference in intra-fiducial distances can be visualized as in FIG. 5A where the arrows 502 point to preoperative fiducials and arrows 506 point to intraoperative fiducials. The maximum intra-fiducial distance difference was distributed evenly among the two control surfaces. A 10 mm displacement was applied to each node on the inferior and superior breast faces. The arrows in FIG. 5B show the direction of the applied displacements. The model corrected FRE was 2.9 mm and the model corrected centroid difference was 5.5 mm. Improved alignment of preoperative and intraoperative tumor contours as a result of non-rigid correction for patient 1 is shown in FIG. 11, which shows an intraoperative ultrasound image with white tumor contour overlaid on preoperative rigid aligned tumors (Top) and non-rigid corrected aligned tumors (Bottom).

Patient 2 Results. Initial rigid alignment for patient subject 2 returned an FRE of 8.8 mm. FIGS. 12A and 12B show results from the rigid registration. The centroid distance between mapped preoperative and intraoperative states before ultrasound compression compensation of the tumor contours was 14.7 mm (illustrated in FIG. 12C). The centroid distance after probe-to-tissue compensation was 12.5 mm (illustrated in FIG. 12D). Following gravitational direction correction, the FRE improved negligibly to 8.5 mm and with a more considerable correction to the centroid distance decreasing to 8.4 mm. As anticipated, principal component analysis following gravity-induced deformation compensation revealed that the largest deformations occurred along the patient's inferior-superior axis. The largest difference in the intra-fiducial distances was 50 mm. The arrows in FIG. 5C show the largest difference in preoperative and intraoperative intra-fiducial distances, respectively. The maximum intra-fiducial distance difference was distributed evenly among the two control surfaces. The green arrows in FIG. 5D point to the direction of applied displacement boundary conditions with a 25 mm displacement applied at each breast face. The non-rigid correction resulted in an FRE of 7.4 mm and centroid distance of 5.4 mm. In FIG. 13, one can observe the improved alignment between MR-rendered tumor and the ultrasound-visible counterpart (white contour) for patient 2.

Discussion. In general, the results show that initial rigid alignments are not sufficient and a non-rigid correction is necessary to obtain a clinically relevant image-to-physical alignment. In each case, arm movement between the preoperative and intraoperative patient setups caused a change in stretch to the breast tissue along the patient's inferior-superior axis. Tissue deformation exerted by the ultrasound probe required correction to improve the fidelity of using tracked ultrasound images of the tumor as a means to assess subsurface target registration error.

Several sources of error may contribute to the reported registration error. The tracking error of the tested system has been reported as sub-millimeter for passively tracked rigid stylus bodies. However, multiple reference targets were attached on range-based targeting devices (laser range scanner and ultrasound). The tracked laser range scanner has been characterized previously at 2.2+/−1.0 mm although its use in this particular work was minimal. With respect to the tracked ultrasound imaging, in studies not reported here we have found our average target registration error to be 1.5-2.5 mm in typical tracking experiments. It is difficult to predict how these errors will combine due to the nature of the registration process. More specifically, our registration approach samples both far-field (chest wall) and near-field (synthetic fiducials) structures which likely constrains internal target error; more study is needed. Other sources of error between MR-localized fiducial and co-localized ink markings in physical space could be present. While some compensation for iUS error was performed, the validation metrics themselves still have some error. The contour digitization of the tumor using tracked ultrasound may not represent a comprehensive digitization of tumor volume and as a result could produce discrepancies of the tumor volume centroid as compared to its preoperative counterpart. In this study, care was taken to acquire ultrasound images of the tumor in orthogonal planes and at multiple angles to best digitize the whole tumor volume. Despite this care, it is unlikely that the measurement is as rigorous as its tomographic counterpart in MR. Another source of error is our use of a linear elastic model for the non-rigid correction of breast tissue. While small-strain approximations are likely violated, we have found linear models to behave reasonably well in such gross non-rigid alignment procedures. In other work, we have compared linear and nonlinear approaches (linear vs co-rotational finite element approaches) with similar registration problems. Observed differences have been modest when compared to the extent of gross misalignment. While all of these errors need further characterization, the results in FIGS. 11 and 13 are difficult to discount. In each, a marked improvement is observed in alignment between the ultrasound-visualized intraoperative tumor contour and the preoperative tumor image.

An exemplary hardware configuration for performing one or more of the methods described above, or any portions thereof, is shown below in FIG. 14. FIG. 14 shows an exemplary hardware system configuration 1400 in accordance with an aspect of the present technology. As shown in FIG. 14, system 1400 can include an image/data processor 1405, a display monitor 1410, and an IGS controller 1415. The IGS controller can be coupled to an optical tracking sensor which consists of sensing optical cameras 1430, and emitters 1420, 1425, and 1435. Further, the IGS controller 1415 can be coupled to one or more emitters that can serve as instruments such as 1420, and 1435. 1440 is a separate computation node controller that interfaces to the image/data processor 1405 for the purpose of non-rigid deformation correction and the aspect of related processes. Although the various components are shown as separate, discrete components, the present technology is not limited in this regard. For example, the IGS controller 1415, the image data processor 1405, and the computation node controller 1440 can be integrated into a single system. Similarly, depending on the nature of correction, the computation node controller 1440 could be separated into multiple computation node controllers networked together.

System 1400 operates as follows. First, emitter 1425 is often affixed to the patient or supporting surgical instrumentation. This could be replaced by providing a fixed camera mount (i.e. fix 1430) within the operating room. Sensor 1430 is used to determine the location of all emitters within the operating room (to include optical stylus 1420, or potentially a laser range scanner 1435). Emitter 1420, or 1435 could be used to detect a surface, or visible structure of a non-rigid organ or the location of an instrument. However, the present technology is not limited in this regard and more than one sensing system can be used to provide surface data and/or instrument/object position data. An example of a system for generating surface data is a laser-range scanner system, such as the RealScan 3D system produced by 3D Digital Corporation of Danbury, Conn. or a similar system custom designed by Pathfinder Therapeutics Inc. of Nashville, Tenn. Such systems are capable of capturing three-dimensional topographic surface data as well surface texture mapping using an array of data points. For example, in one aspect a scanning field of 500 horizontal by 512 vertical points can be acquired in 5-10 seconds and used to generate surface data of exposed surfaces during IGS procedures. In some aspects, such a system can be tracked in the operating room space using a digitization system and calibrated using phantoms with separate independent digitization. 1435 would represent the result of their use. One advantage of this laser-range scanner system over other surface digitization techniques is the capability of capturing feature-rich texture maps of the surface as well as the topographical characteristics. Such texture map data generally facilitates the segmentation, i.e. extraction, of the liver surface for alignment to preoperative imaging. Other aspects could use a tracked ultrasound probe which could acquire external and/or interior surface data. The data could be used to extract any number of boundary data to include external and/or interior surface structures for use in the alignment process.

Figure 1B:
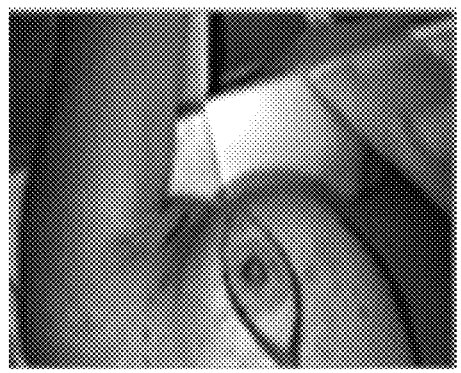
Figure 1A:
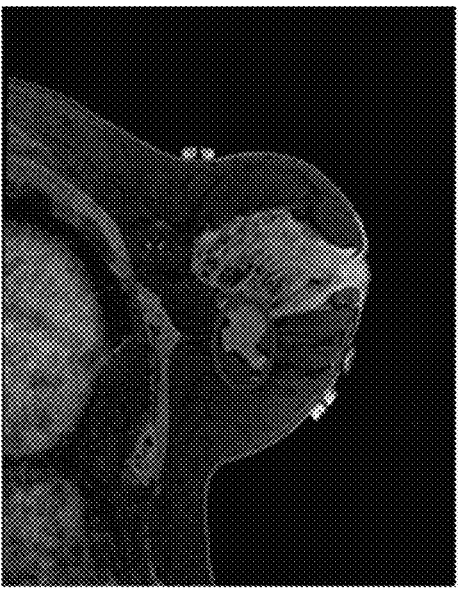

In operation, system 1400 operates as follows. Prior to surgery, relevant data regarding the preoperative organ 102 would be transmitted to the computation node controller 1440 or would have been processed on the controller 1415. Upon collection of surface data from digitization equipment like that of 1420 and 1435, the image/data processor 1405 transmits that data as well as any other relevant intraoperative information to the computation node controller 1440. Using the computer model, the computation node controller 1440 completes the rigid alignment of the computer model to the surface data, as described in FIG. 1, followed by the non-rigid alignment of the computer model to the surface data, as described in FIGS. 1 and 2. Data/image processor 1405 may also perform transformations on the data. As described above, a local transformation may also be required. In such cases, the computation node controller 1440 can generate such deformed and adjusted maps, as described above with respect to FIG. 5. The map can then be used to perform IGS procedures either by transforming points on the computation node controller 1440, or by providing the proper mapping function to the data/image processing unit 1405 and allowing it to apply the proper transform for the IGS display 1410.

Figure 15A:
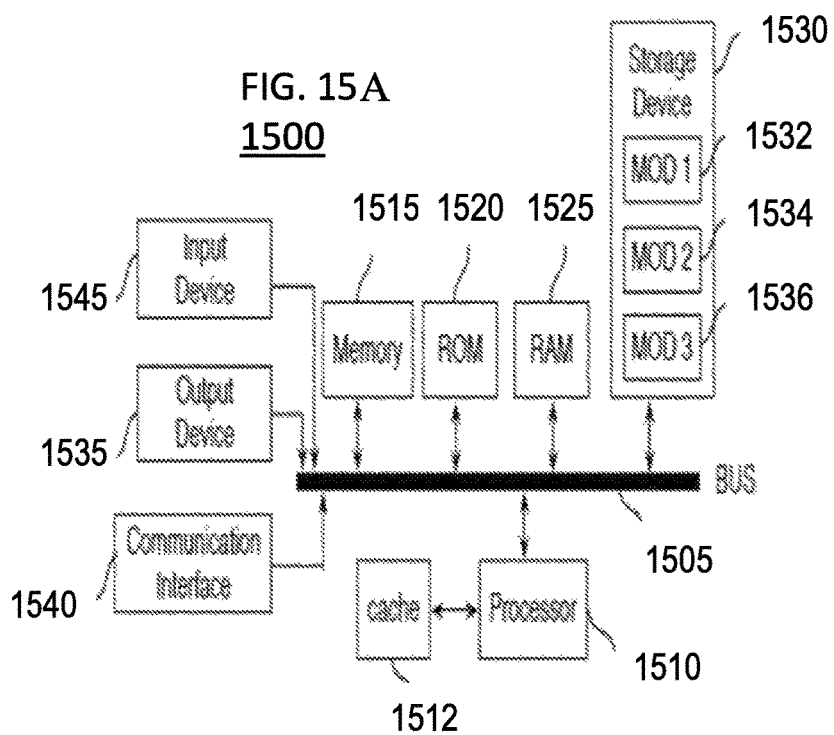
FIG. 15A and FIG. 15B illustrate exemplary possible system configurations for implementing the present technology.
Figure 15B:
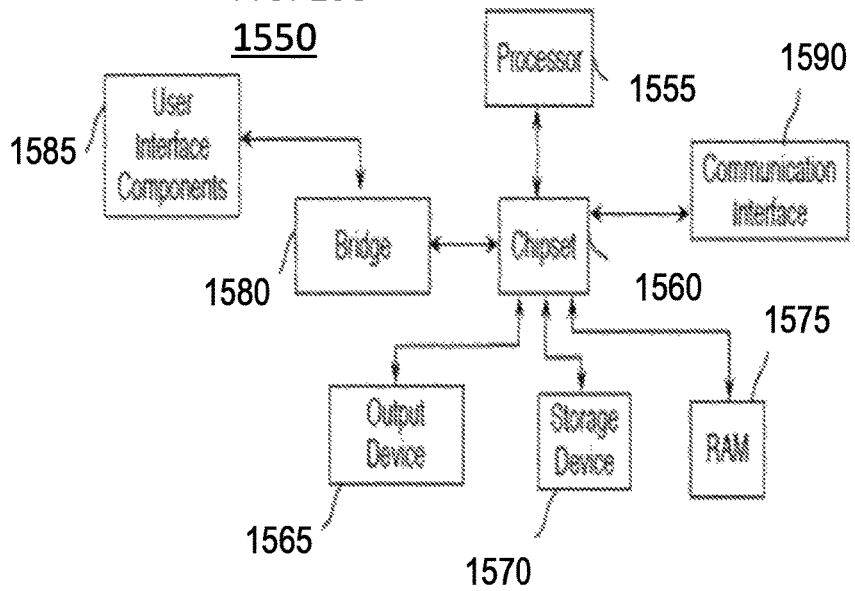

FIG. 15A and FIG. 15B illustrate exemplary possible system configurations. The more appropriate configuration will be apparent to those of ordinary skill in the art when practicing the present technology. Persons of ordinary skill in the art will also readily appreciate that other system configurations are possible.

FIG. 15A illustrates a conventional system bus computing system architecture 1500 wherein the components of the system are in electrical communication with each other using a bus 1505. Exemplary system 1500 includes a processing unit (CPU or processor) 1510 and a system bus 1505 that couples various system components including the system memory 1515, such as read only memory (ROM) 1520 and random access memory (RAM) 1525, to the processor 1510. The system 1500 can include a cache of high-speed memory connected directly with, in close proximity to, or integrated as part of the processor 1510. The system 1500 can copy data from the memory 1515 and/or the storage device 1530 to the cache 1512 for quick access by the processor 1510. In this way, the cache can provide a performance boost that avoids processor 1510 delays while waiting for data. These and other modules can control or be configured to control the processor 1510 to perform various actions. Other system memory 1515 may be available for use as well. The memory 1515 can include multiple different types of memory with different performance characteristics. The processor 1510 can include any general purpose processor and a hardware module or software module, such as module 1 1532, module 2 1534, and module 3 1536 stored in storage device 1530, configured to control the processor 1510 as well as a special-purpose processor where software instructions are incorporated into the actual processor design. The processor 1510 may essentially be a completely self-contained computing system, containing multiple cores or processors, a bus, memory controller, cache, etc. A multi-core processor may be symmetric or asymmetric.

To enable user interaction with the computing device 1500, an input device 1545 can represent any number of input mechanisms, such as a microphone for speech, a touch-sensitive screen for gesture or graphical input, keyboard, mouse, motion input, speech and so forth. An output device 1535 can also be one or more of a number of output mechanisms known to those of skill in the art. In some instances, multimodal systems can enable a user to provide multiple types of input to communicate with the computing device 1500. The communications interface 1540 can generally govern and manage the user input and system output. There is no restriction on operating on any particular hardware arrangement and therefore the basic features here may easily be substituted for improved hardware or firmware arrangements as they are developed.

Storage device 1530 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1525, read only memory (ROM) 1520, and hybrids thereof.

The storage device 1530 can include software modules 1532, 1534, 1536 for controlling the processor 1510. Other hardware or software modules are contemplated. The storage device 1530 can be connected to the system bus 1505. In one aspect, a hardware module that performs a particular function can include the software component stored in a computer-readable medium in connection with the necessary hardware components, such as the processor 1510, bus 1505, display 1535, and so forth, to carry out the function.

FIG. 15B illustrates a computer system 1550 having a chipset architecture that can be used in executing the described method and generating and displaying a graphical user interface (GUI). Computer system 1550 is an example of computer hardware, software, and firmware that can be used to implement the disclosed technology. System 1550 can include a processor 1555, representative of any number of physically and/or logically distinct resources capable of executing software, firmware, and hardware configured to perform identified computations. Processor 1555 can communicate with a chipset 1560 that can control input to and output from processor 1555. In this example, chipset 1560 outputs information to output 1565, such as a display, and can read and write information to storage device 1570, which can include magnetic media, and solid state media, for example. Chipset 1560 can also read data from and write data to RAM 1575. A bridge 1580 for interfacing with a variety of user interface components 1585 can be provided for interfacing with chipset 1560. Such user interface components 1585 can include a keyboard, a microphone, touch detection and processing circuitry, a pointing device, such as a mouse, and so on. In general, inputs to system 1550 can come from any of a variety of sources, machine generated and/or human generated.

Chipset 1560 can also interface with one or more communication interfaces 1590 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 1555 analyzing data stored in storage 1570 or 1575. Further, the machine can receive inputs from a user via user interface components 1585 and execute appropriate functions, such as browsing functions by interpreting these inputs using processor 1555.

It can be appreciated that exemplary systems 1500 and 1550 can have more than one processor 1510 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some configurations the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims. Claim language reciting "at least one of" a set indicates that one member of the set or multiple members of the set satisfy the claim. Tangible computer-readable storage media, computer-readable storage devices, or computer-readable memory devices, expressly exclude media such as transitory waves, energy, carrier signals, electromagnetic waves, and signals per se.

While various aspects of the present technology have been described above, it should be understood that they have been presented by way of example only, and not limitation. Numerous changes to the disclosed aspects can be made in accordance with the disclosure herein without departing from the spirit or scope of the present technology. Thus, the breadth and scope of the present technology should not be limited by any of the above described aspects. Rather, the scope of the present technology should be defined in accordance with the following claims and their equivalents.

Although the present technology has been illustrated and described with respect to one or more implementations, equivalent alterations and modifications will occur to others skilled in the art upon the reading and understanding of this specification and the annexed drawings. In addition, while a particular feature of the present technology may have been disclosed with respect to only one of several implementations, such feature may be combined with one or more other features of the other implementations as may be desired and advantageous for any given or particular application.

The terminology used herein is for the purpose of describing particular aspects only and is not intended to be limiting of the present technology. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this present technology belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method of performing image-guided surgery, comprising:
    obtaining intraoperative location data for a patient comprising intraoperative fiducial location data for a non-rigid structure of interest in the patient and intraoperative rigid structure location data for at least one rigid structure in the patient associated with the non-rigid structure;
    estimating a gravity deformation for the non-rigid structure of interest based on a first rigid registration for preoperative fiducial location data in a preoperative computer model of the patient with respect to the intraoperative fiducial location data and a second rigid registration for the preoperative rigid structure location data for at least one rigid structure in the computer model with respect to the intraoperative rigid structure location data;
    modifying the preoperative fiducial location data using first rigid registration and the gravity deformation to yield modified fiducial location data;
    determining a third rigid registration comprising a rigid registration for the modified fiducial location data with respect to the intraoperative fiducial location data;
    calculating a non-rigid transformation for the computer model based on the volumetric gravity field deformation and first boundary conditions derived from errors in the third rigid registration;

displaying deformed image data comprising preoperative image data corresponding to the computer modified to undergo the non-rigid transformation.

2. The method of claim 1, wherein the estimating comprises:
determining a gravity vector rotation based on a comparison of the first rigid registration and the second rigid registration; and
computing the volumetric gravity field deformation using the gravity vector location and a three-dimensional elastic model.

3. The method of claim 2, wherein the computing comprises a finite element analysis.

4. The method of claim 1, wherein the modifying comprises:
applying a transformation based on the first rigid registration to at least a portion of the computer model corresponding to the non-rigid structure to yield a modified computer model;
performing a finite element analysis for the modified computer model based on the gravity deformation and second boundary conditions to yield the modified fiducial data,
wherein the second boundary conditions specify that nodes of the modified computer model associated with the portion and adjacent to the at least one rigid structure are fixed and other nodes of the portion are stress-free.

5. The method of claim 1, wherein the calculating comprises:
performing a principal components analysis (PCA) on the errors in a transformation corresponding the third rigid registration to extract a PCA error vector describing principal components of the errors in the third rigid registration; and
computing the boundary conditions based on the PCA error vector.

6. The method of claim 1, wherein the calculating comprises performing a finite element registration for the computer model with respect to the intraoperative location data subject to the volumetric gravity field deformation and the boundary conditions to yield the non-rigid transformation.

7. The method of claim 1, prior to the displaying repeating, using the computer model modified to undergo the non-rigid transformation, the obtaining, estimating, modifying, determining, and calculating.

8. The method of claim 1, wherein the intraoperative location data comprises intraoperative shape data for the non-rigid structure, wherein the computer model comprises preoperative shape data for the non-rigid structure, and wherein at least one of the first rigid registration, the second rigid registration, and the third rigid registration further involve a registration of the preoperative shape data with respect to the intraoperative shape data.

9. The method of claim 1, further comprising performing, prior to the displaying, the steps of:
assessing an alignment error of the non-rigid transformation for the computer model with respect to the intraoperative fiducial location data;
detecting that the alignment error is outside a pre-defined error tolerance; and
in response to detecting that the alignment error is outside the pre-defined error tolerance, updating the first boundary conditions; and
repeating the calculating, assessing, detecting and updating until the alignment error is within the pre-defied error tolerance or another termination condition has been met.

10. A non-transitory computer-readable medium, having stored thereon a computer program executable by a computing device, the computer program comprising a plurality of code sections for performing the method comprising:
obtaining intraoperative location data for a patient comprising intraoperative fiducial location data for a non-rigid structure of interest in the patient and intraoperative rigid structure location data for at least one rigid structure in the patient associated with the non-rigid structure;
estimating a gravity deformation for the non-rigid structure of interest based on a first rigid registration for preoperative fiducial location data in a preoperative computer model of the patient with respect to the intraoperative fiducial location data and a second rigid registration for the preoperative rigid structure location data for at least one rigid structure in the computer model with respect to the intraoperative rigid structure location data;
modifying the preoperative fiducial location data using first rigid registration and the gravity deformation to yield modified fiducial location data;
determining a third rigid registration comprising a rigid registration for the modified fiducial location data with respect to the intraoperative fiducial location data;
calculating a non-rigid transformation for the computer model based on the volumetric gravity field deformation and first boundary conditions derived from errors in the third rigid registration;
displaying deformed image data comprising preoperative image data corresponding to the computer modified to undergo the non-rigid transformation.

11. The non-transitory computer-readable medium of claim 10, wherein the estimating comprises:
determining a gravity vector rotation based on a comparison of the first rigid registration and the second rigid registration; and
computing the volumetric gravity field deformation using the gravity vector location and a three-dimensional elastic model.

12. The non-transitory computer-readable medium of claim 11, wherein the computing comprises a finite element analysis.

13. The non-transitory computer-readable medium of claim 10, wherein the modifying comprises:
applying a transformation based on the first rigid registration to at least a portion of the computer model corresponding to the non-rigid structure to yield a modified computer model;
performing a finite element analysis for the modified computer model based on the gravity deformation and second boundary conditions to yield the modified fiducial data,
wherein the second boundary conditions specify that nodes of the modified computer model associated with the portion and adjacent to the at least one rigid structure are fixed and other nodes of the portion are stress-free.

14. The non-transitory computer-readable medium of claim 10, wherein the calculating comprises:
performing a principal components analysis (PCA) on the errors in a transformation corresponding the third rigid registration to extract a PCA error vector describing principal components of the errors in the third rigid registration; and computing the boundary conditions based on the PCA error vector.

15. The non-transitory computer-readable medium of claim 10, wherein the calculating comprises performing a finite element registration for the computer model with respect to the intraoperative location data subject to the volumetric gravity field deformation and the boundary conditions to yield the non-rigid transformation.

16. A system for performing image-guided surgery, comprising:

a sensing system configured to measure physical space and configured to obtain intraoperative location data for a patient comprising intraoperative fiducial location data for a non-rigid structure of interest in the patient and intraoperative rigid structure location data for at least one rigid structure in the patient associated with the non-rigid structure;

a display device;

a storage medium for storing preoperative computer model of the patient, a computer model of a non-rigid structure of interest in a patient corresponding to the preoperative image, and the surface data, the computer model comprising a plurality of nodes; and a processing element communicatively coupled to the sensing system, the display device, and the storage medium, wherein the processing element is configured for:

estimating a gravity deformation for the non-rigid structure of interest based on a first rigid registration for preoperative fiducial location data in the preoperative computer model with respect to the intraoperative fiducial location data and a second rigid registration for the preoperative rigid structure location data for at least one rigid structure in the computer model with respect to the intraoperative rigid structure location data;

modifying the preoperative fiducial location data using first rigid registration and the gravity deformation to yield modified fiducial location data;

determining a third rigid registration comprising a rigid registration for the modified fiducial location data with respect to the intraoperative fiducial location data;

calculating a non-rigid transformation for the computer model based on the volumetric gravity field deformation and first boundary conditions derived from errors in the third rigid registration;

displaying deformed image data comprising preoperative image data corresponding to the computer modified to undergo the non-rigid transformation.

17. The system of claim 16, wherein the estimating comprises:

determining a gravity vector rotation based on a comparison of the first rigid registration and the second rigid registration; and computing the volumetric gravity field deformation using the gravity vector location and a three-dimensional elastic model.

18. The system of claim 16, wherein the modifying comprises:

applying a transformation based on the first rigid registration to at least a portion of the computer model corresponding to the non-rigid structure to yield a modified computer model;

performing a finite element analysis for the modified computer model based on the gravity deformation and second boundary conditions to yield the modified fiducial data, wherein the second boundary conditions specify that nodes of the modified computer model associated with the portion and adjacent to the at least one rigid structure are fixed and other nodes of the portion are stress-free.

19. The system of claim 16, wherein the calculating comprises:

performing a principal components analysis (PCA) on the errors in a transformation corresponding the third rigid registration to extract a PCA error vector describing principal components of the errors in the third rigid registration; and computing the boundary conditions based on the PCA error vector.

20. The system of claim 16, wherein the calculating comprises performing a finite element registration for the computer model with respect to the intraoperative location data subject to the volumetric gravity field deformation and the boundary conditions to yield the non-rigid transformation.

* * * * *